(12) United States Patent
Na et al.

(10) Patent No.: US 8,979,912 B2
(45) Date of Patent: Mar. 17, 2015

(54) METHOD, SYSTEM, AND APPARATUS FOR DERMALOGICAL TREATMENT

(76) Inventors: Jongju Na, Seoul (KR); Merle Richman, La Jolla, CA (US)

(*) Notice: Subject to any disclaimer, the term of this patent is extended or adjusted under 35 U.S.C. 154(b) by 643 days.

(21) Appl. No.: 13/060,274

(22) PCT Filed: Aug. 22, 2008

(86) PCT No.: PCT/US2008/074131
§ 371 (c)(1),
(2), (4) Date: Mar. 30, 2011

(87) PCT Pub. No.: WO2010/016848
PCT Pub. Date: Feb. 11, 2010

(65) Prior Publication Data
US 2011/0172745 A1    Jul. 14, 2011

(30) Foreign Application Priority Data
Aug. 8, 2008 (KR) .................. 10-2008-0076993 0

(51) Int. Cl.
| A61N 5/06 | (2006.01) |
| A61H 15/02 | (2006.01) |
| A61H 39/00 | (2006.01) |
| A61M 37/00 | (2006.01) |
| A61H 23/02 | (2006.01) |
| A61H 15/00 | (2006.01) |

(52) U.S. Cl.
CPC .............. *A61N 5/0616* (2013.01); *A61H 15/02* (2013.01); *A61H 23/02* (2013.01); *A61H 39/002* (2013.01); *A61H 2015/0014* (2013.01); *A61H 2039/005* (2013.01); *A61H 2201/0153* (2013.01); *A61H 2201/1604* (2013.01); *A61H 2201/169* (2013.01); *A61H 2201/5097* (2013.01); *A61H 2205/022* (2013.01); *A61H 2205/04* (2013.01); *A61H 2205/06* (2013.01); *A61H 2205/065* (2013.01); *A61H 2205/084* (2013.01); *A61H 2205/10* (2013.01); *A61H 2205/12* (2013.01); *A61M 37/00* (2013.01); *A61N 2005/0644* (2013.01); *A61N 2005/0652* (2013.01)
USPC .................. 607/88; 604/20; 604/46; 604/21; 604/117; 606/9; 601/2; 424/1.11; 607/102; 607/189

(58) Field of Classification Search
USPC ................. 604/20, 46, 21, 117; 606/9; 601/2; 424/1.11; 607/102, 189
See application file for complete search history.

(56) References Cited

U.S. PATENT DOCUMENTS

| 6,931,277 | B1* | 8/2005 | Yuzhakov et al. ............... 604/21 |
| 7,133,717 | B2* | 11/2006 | Coston et al. .................... 604/20 |
| 7,824,394 | B2* | 11/2010 | Manstein .......................... 606/9 |
| 2006/0047295 | A1* | 3/2006 | Abramov ....................... 606/189 |
| 2007/0073217 | A1* | 3/2007 | James ............................. 604/46 |
| 2007/0142885 | A1* | 6/2007 | Hantash et al. ................ 607/102 |
| 2007/0231255 | A1* | 10/2007 | Barolet et al. ................ 424/1.11 |
| 2007/0232962 | A1* | 10/2007 | Zumeris et al. .................... 601/2 |
| 2007/0276318 | A1* | 11/2007 | Henley ............................ 604/20 |
| 2008/0114298 | A1* | 5/2008 | Cantor et al. .................. 604/117 |

* cited by examiner

*Primary Examiner* — William Thomson
*Assistant Examiner* — Victor Shapiro
(74) *Attorney, Agent, or Firm* — Merle W. Richman, Esq.

(57) ABSTRACT

Embodiments of dermalogical cell treatment are described generally herein. Other embodiments may be described and claimed.

20 Claims, 13 Drawing Sheets

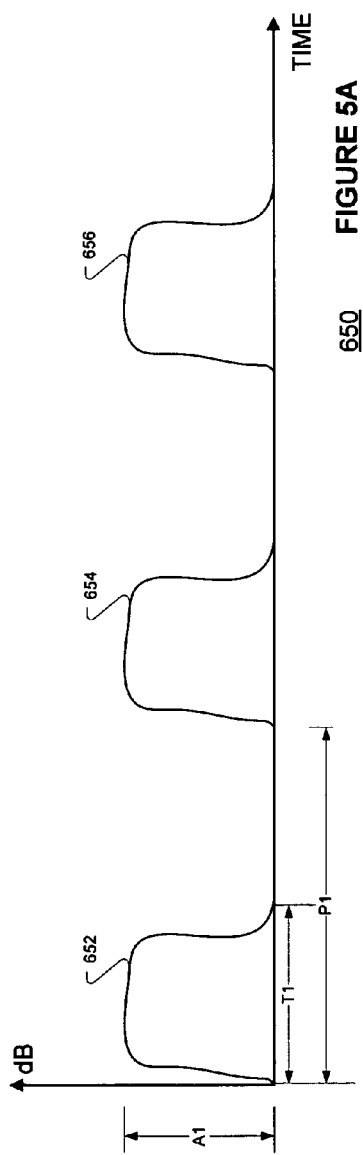
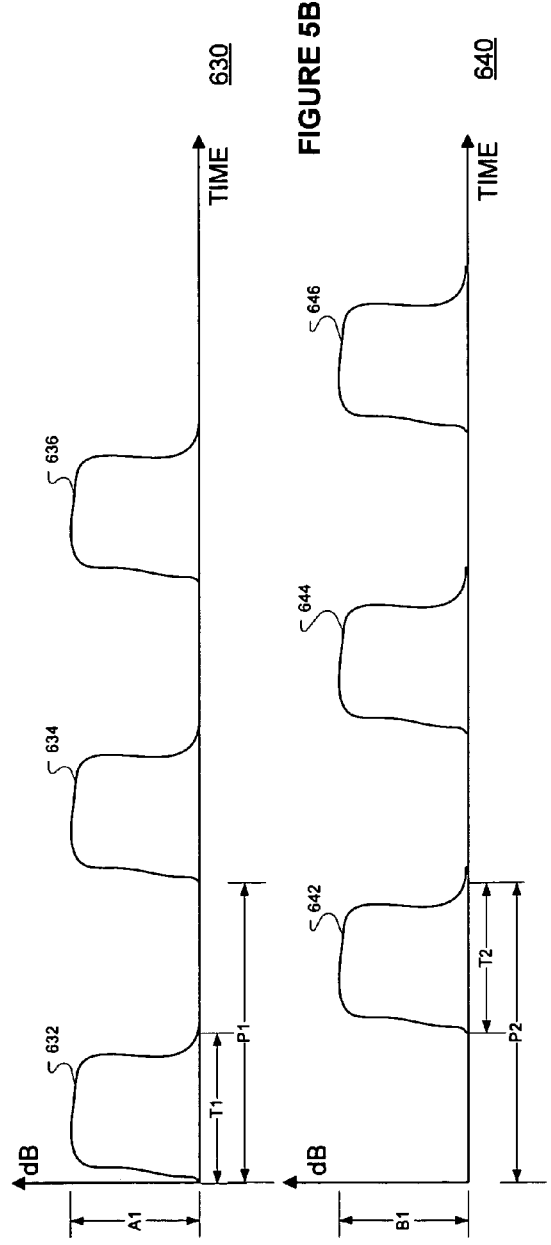

METHOD, SYSTEM, AND APPARATUS FOR DERMALOGICAL TREATMENT

CROSS REFERENCE TO RELATED APPLICATIONS

The present application claims the benefit of priority to Republic of Korea Application Number 10-2008-0076993, entitled "Electrical system, skin, skin care and cosmetic electricity," filed on Aug. 8, 2008, the entirety of which is incorporated by reference.

TECHNICAL FIELD

Various embodiments described herein relate generally to treating dermalogical tissue, including systems, and methods used in treating dermalogical tissue.

BACKGROUND INFORMATION

It may be desirable to treat dermalogical tissue, the present invention provides such treatment.

BRIEF DESCRIPTION OF THE DRAWINGS

FIG. 5A-6 are diagrams of signals that may be applied to one or more dermalogical treatment systems according to various embodiments.

DETAILED DESCRIPTION

Figure 1B:
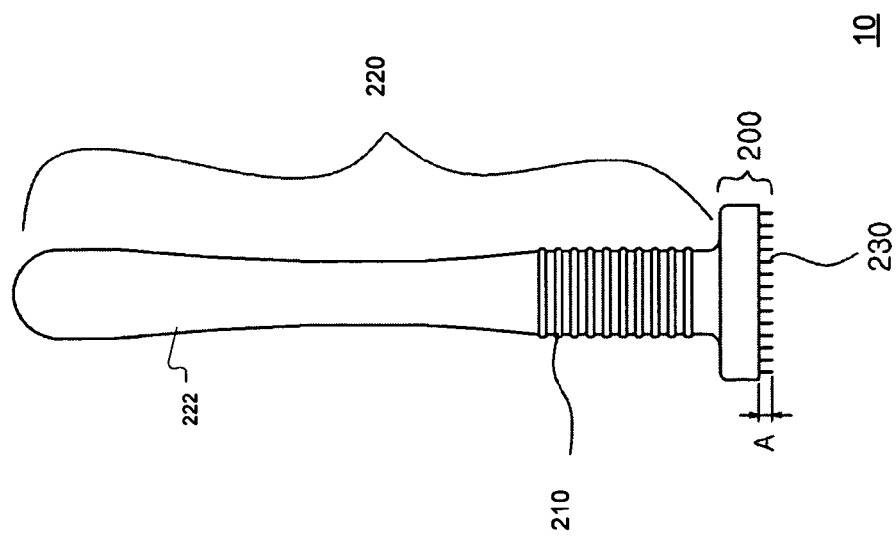
FIG. 1B is a simplified, side diagram of the dermalogical treatment apparatus according to various embodiments.
Figure 1A:
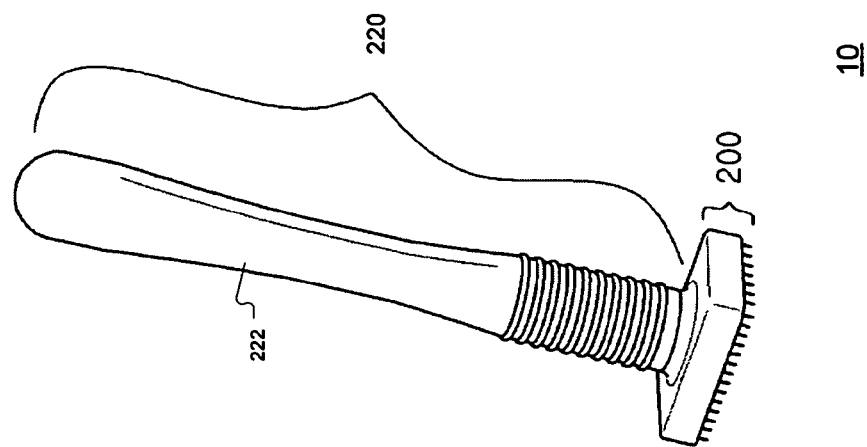
FIG. 1A is a simplified isometric diagram of a dermalogical treatment apparatus according to various embodiments.

FIG. 1A is a simplified isometric diagram and FIG. 1B is a simplified side view of a dermalogical treatment apparatus 10 according to various embodiments. The apparatus 10 may include a user handle 220 coupled to an acupuncture plate 200. In an embodiment the plate 200 may be elastically coupled to the handle segment 222 via an elastomeric section 210. The elastomeric section may be comprised of a combination of elastomeric materials and non-elastomeric materials. The elastomeric materials may include plastics, rubber (synthetic or natural), and spring(s).

Figure 1D:
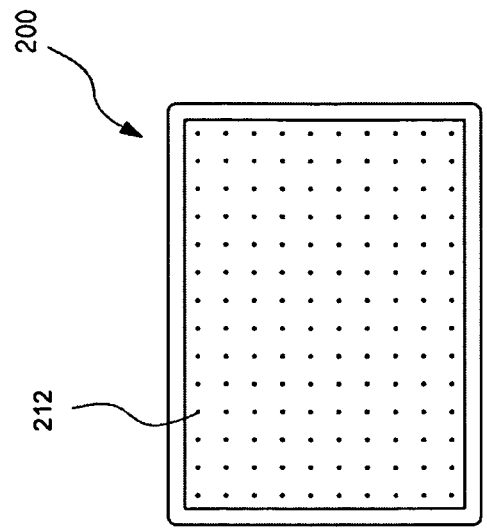
FIG. 1D is a simplified view of a layer of a dermalogical treatment apparatus according to various embodiments.
Figure 1C:
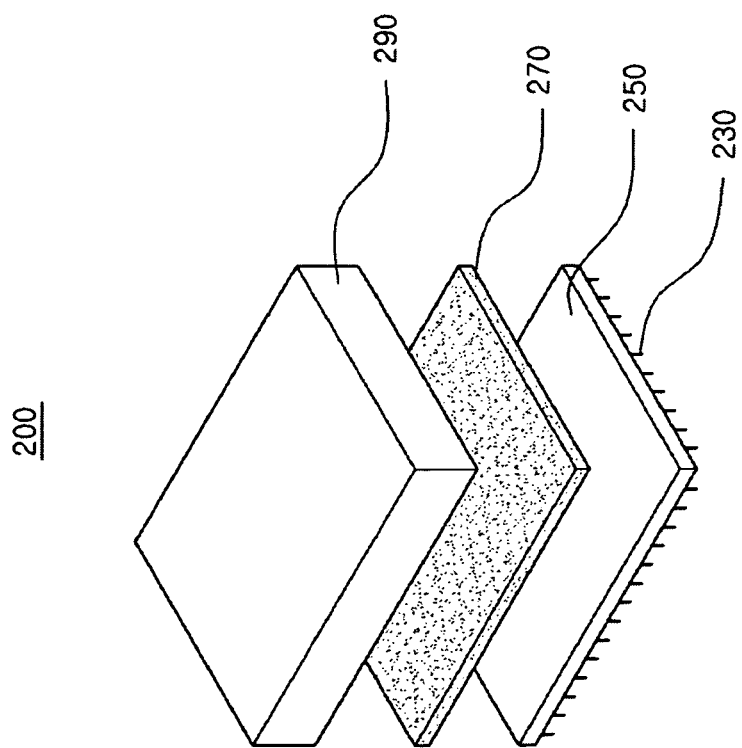
FIG. 1C is a simplified, exploded view of layers of the dermalogical treatment apparatus according to various embodiments.

FIG. 1C includes a simplified exploded view of an embodiment of an acupuncture plate 200 according to various embodiments. The plate 200 may include an upper, substantially rigid section or layer 290, deformable or elastic section 270 or layer, and acupuncture section or layer 250. The acupuncture section 250 may include a plurality of acupuncture pins or needles 230. FIG. 1D is a simplified bottom view of the plate 200 showing the location or holes 212 for the pins or needles 230. In an embodiment the plate 200 may have a rectangular cross section having a dimensional about 1 to 4 cm in width and about 1 to 6 cm in length. The plate 200 may any shape including circular, elliptical, polygon, or other shape where the shape may be particular to a dermalogical area to be treated.

In an embodiment the plate may include about 140 pins or needles 230 uniformly separated. Each needle may be about 0.1 to 0.4 mm in diameter and 0.2 mm to 1.4 mm in length including 0.3 mm in diameter and 0.8 mm in length in an embodiment. The elastic section or layer 270 may be comprised of a combination of elastomeric materials and non-elastomeric materials. The elastomeric materials may include plastics, rubber (synthetic or natural), and spring(s). The pin section 230 may be coupled directly or indirectly to the upper section 290 via the elastic section 250, including via glues, screws, welds, or other connection. In an embodiment the pin section 250 may include elastomers to enable at least partial deformation of the pin section 250 about the pins 230.

In operation a user may employ the apparatus 10 to create a plurality of micro-wounds or holes in dermalogical layers of a mammal's 20 skin or dermis. The micro-wound or hole creation may improve the absorption or application of one or more chemicals applied on or about the micro-wounds or holes.

Figure 2A:
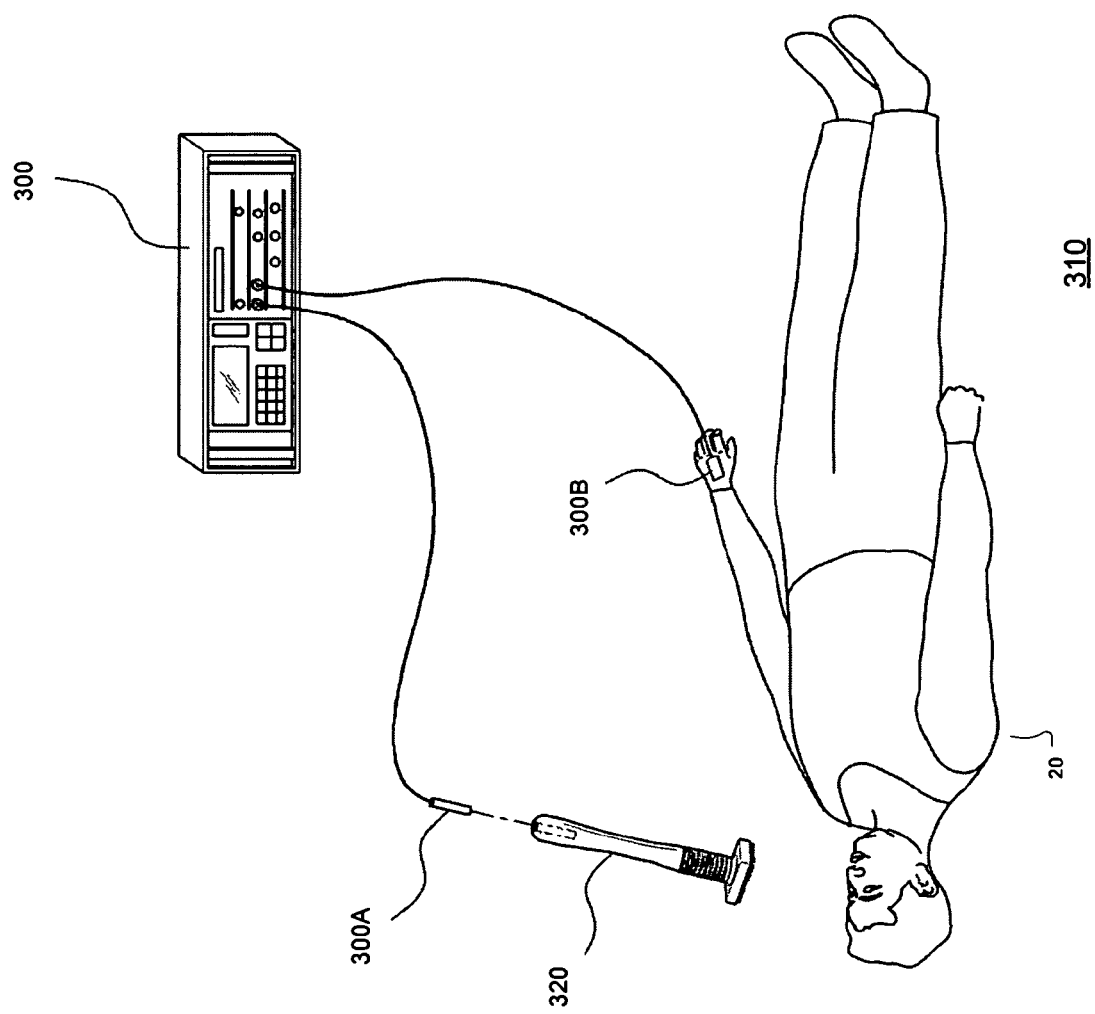
FIG. 2A is a simplified isometric diagram of a dermalogical treatment architecture according to various embodiments.
Figures 2B, 2C:
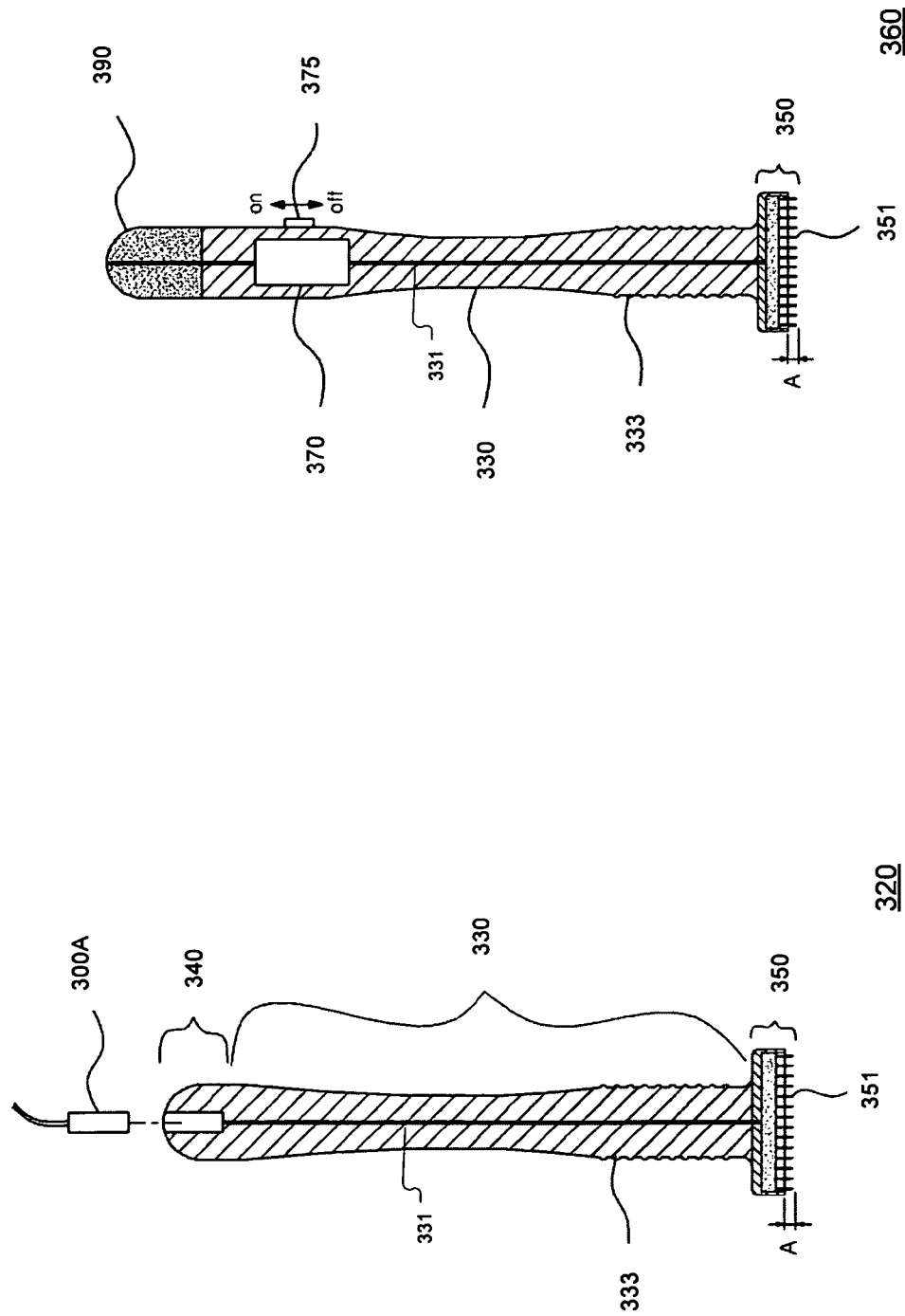
FIG. 2B is a simplified cross-sectional diagram of a dermalogical treatment apparatus according to various embodiments.
FIG. 2C is a simplified cross-sectional diagram of another dermalogical treatment apparatus according to various embodiments.

FIG. 2A is a simplified diagram of a dermalogical treatment architecture 310 according to various embodiments. Architecture 310 includes an acupuncture apparatus 320 and an electrical signal generation system 300. The electrical signal generation system 300 may be electrically coupled to the acupuncture apparatus 320 via one or more wires 300A and to a mammal 20 to be treated via one or more wires 300B. FIG. 2B is a simplified cross-sectional diagram of the acupuncture apparatus 320 according to various embodiments. The apparatus 320 may include a handle 330, elastic section 333, electrical interface 340, internal wire(s) 331 and plate 350. The pins 351 may have a length A (0.3 mm to 2.1 mm in an embodiment) where at least one pin 351 is electrically coupled to the electrical interface 340 via the internal wire 331. The electrical interface 340 may be removably connected to the system 300 wire 300A.

Figure 6:
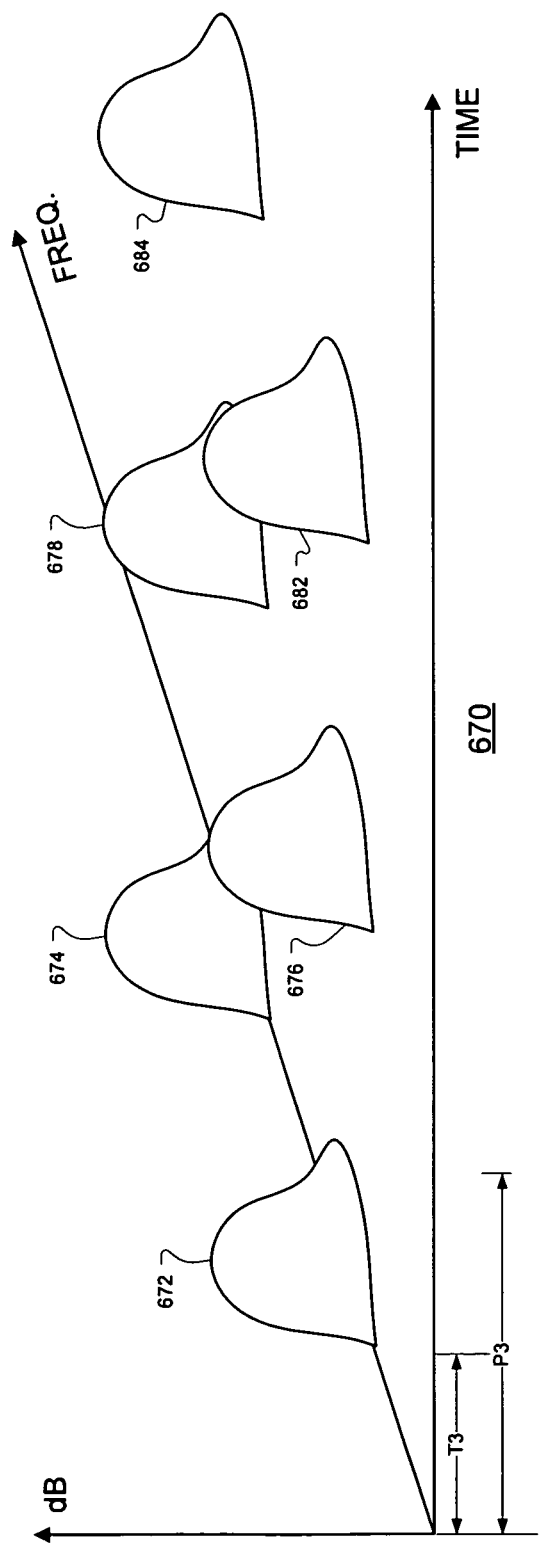

The electrical signal generation system 300 may generate a vary of signals (such as shown in FIGS. 5A to 6) to vibrate one or more pins 351 electrically coupled to the system 300 via the internal wire 331 and lead 300A. A pin vibration 351 may increase the micro-wound or cut formed in dermis by the pin 351. FIG. 2C is a simplified cross-sectional diagram of an acupuncture apparatus 360 according to various embodiments. The apparatus 360 may include a handle 330, an elastic section 333, an electrical conductive interface 390, internal wire(s) 331, signal generator 370, switch 375, and plate 350. The signal generator 370 may be coupled to at least one pin 351 via internal wire 331 and coupled to the conductive interface 390.

The signal generator or module 370 may generate a vary of signals (such as shown in FIGS. 5A to 6) to vibrate one or more pins 351 electrically coupled to the system 300 via the internal wire 331 and the conductive interface 390. In operation a user 20 may touch the conductive interface 390 and place one or more electrically coupled pins 351 in contact with their dermis to form an electrical pathway from the pin 351 to the electrical conductive interface 390. The signal generator 370 may include a battery to supply energy to generate one or more electrical signals. The switch 375 coupled to the generator 370 may cause the generator to produce one or more electrical signals for a predetermined time interval or until the switch 375 is triggered again. As noted a pin vibration 351 may increase the micro-wound or cut formed in dermis by the pin 351.

Figure 2D:
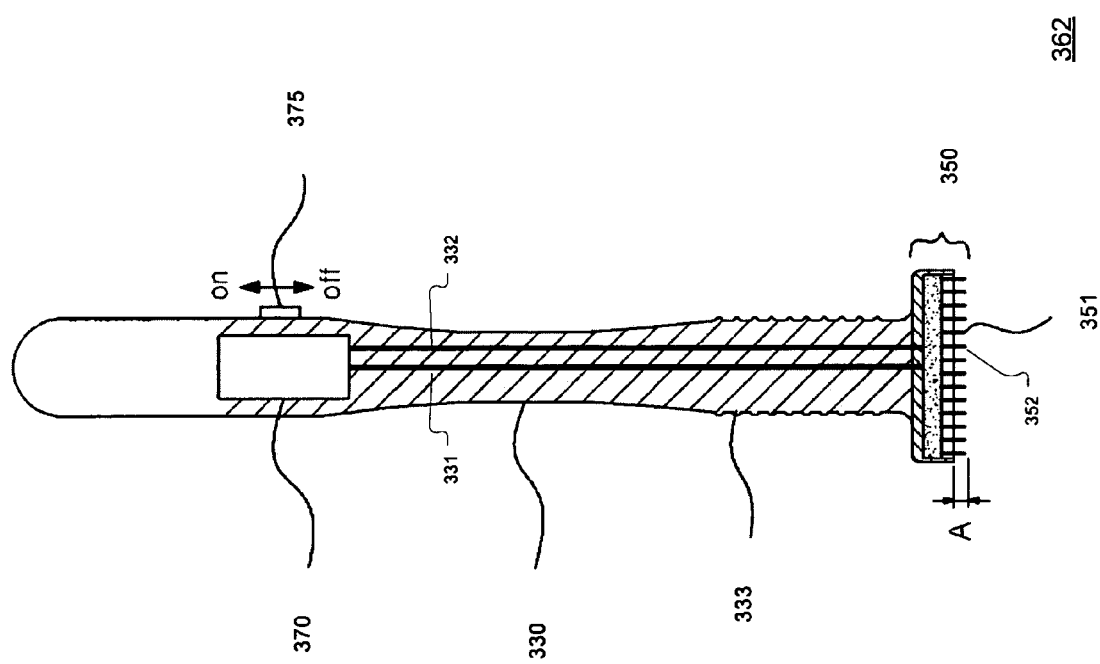
FIG. 2D is a simplified cross-sectional diagram of another dermalogical treatment apparatus according to various embodiments.

FIG. 2D is a simplified cross-sectional diagram of an acupuncture apparatus 362 according to various embodiments. The apparatus 362 may include a handle 330, an elastic section 333, internal wire(s) 331, 332, signal generator 370, switch 375, and plate 350. The signal generator 370 may be coupled to at least one pin 351 via internal wire 331 and coupled to at least one other pin 352 via internal wire 332. When active the pins 351, 352 may form at least one dipole pair. The signal generator or module 370 may generate a vary of signals (such as shown in FIGS. 5A to 6) to vibrate one or more dipole pair or bipolar pins 351, 352.

Figure 2F:
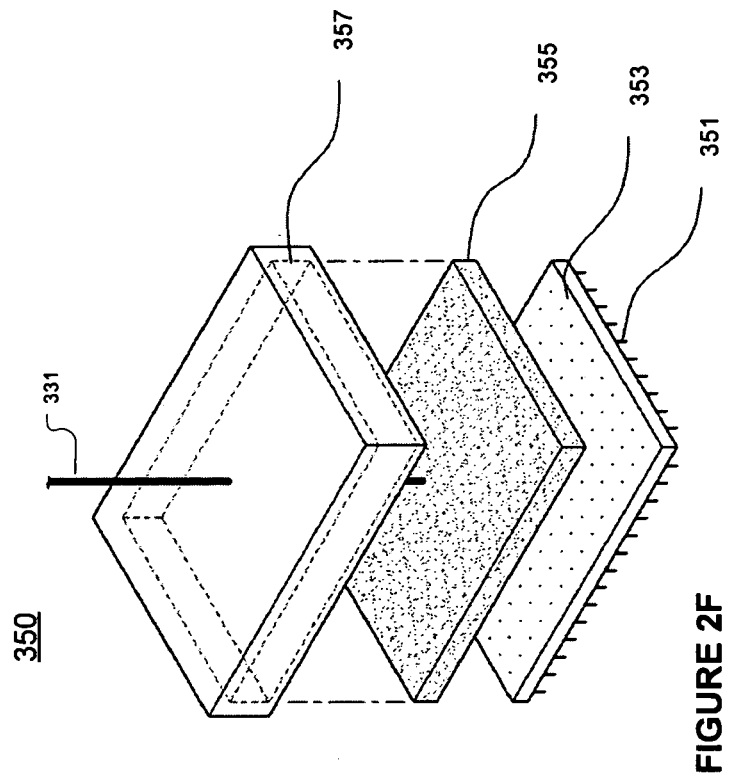
FIG. 2F is a simplified, exploded view of layers of the dermalogical treatment apparatus according to various embodiments.
Figure 2E:
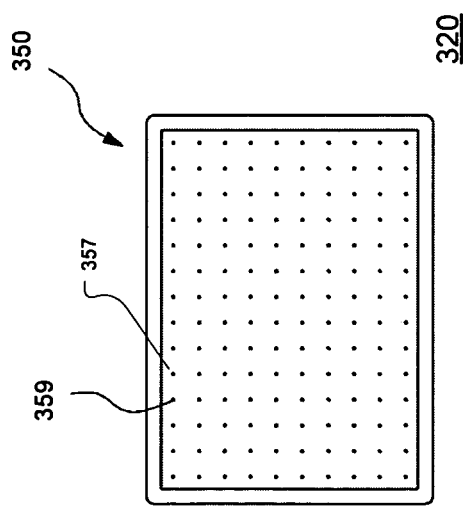
FIG. 2E is a simplified view of a layer of a dermalogical treatment apparatus according to various embodiments.

FIG. 2F includes a simplified exploded view of an embodiment of an acupuncture plate 350 including at least one electrically coupled pin 351 according to various embodiments. The plate 350 may include an upper, substantially rigid section or layer 357, deformable or elastic section 355 or layer, and acupuncture section or layer 353. The acupuncture section 353 may include a plurality of acupuncture pins or needles 351 where at least one pin 351 is electrically coupled to the wire 331. In a bipolar configuration a second wire 332 may be coupled to at least one other pin 351. FIG. 2E is a simplified bottom view of the plate 350 showing the pins or needles 359, 357 where the pins may be electrically coupled to a first wire 331 and a second wire 332 to form dipole pair (bipolar pins).

In an embodiment the plate 350 may have a rectangular cross section having a dimensional about 1 to 4 cm in width and about 1 to 6 cm in length. The plate 350 may any shape including circular, elliptical, polygon, or other shape where the shape may be particular to a dermalogical area to be treated.

In an embodiment the plate may include about 140 pins or needles 351 uniformly separated. Each needle may be about 0.1 to 0.4 mm in diameter and 0.2 mm to 1.4 mm in length including 0.3 mm in diameter and 0.8 mm in length in an embodiment. The elastic section or layer 355 may be comprised of a combination of elastomeric materials and non-elastomeric materials. The elastomeric materials may include plastics, rubber (synthetic or natural), and spring(s). The pin section 353 may be coupled directly or indirectly to the upper section 357 via the elastic section 353, including via glues, screws, welds, or other connection. In an embodiment the pin section 353 may include elastomers to enable at least partial deformation of the pin section 353 about the pins 351.

Figure 3B:
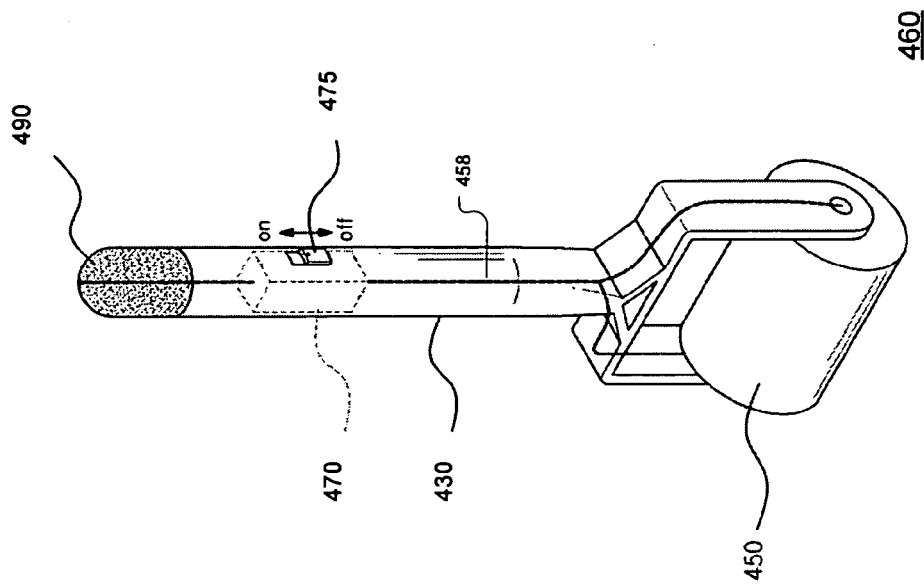
FIG. 3B is a simplified isometric diagram of another dermalogical treatment apparatus according to various embodiments.
Figure 3A:
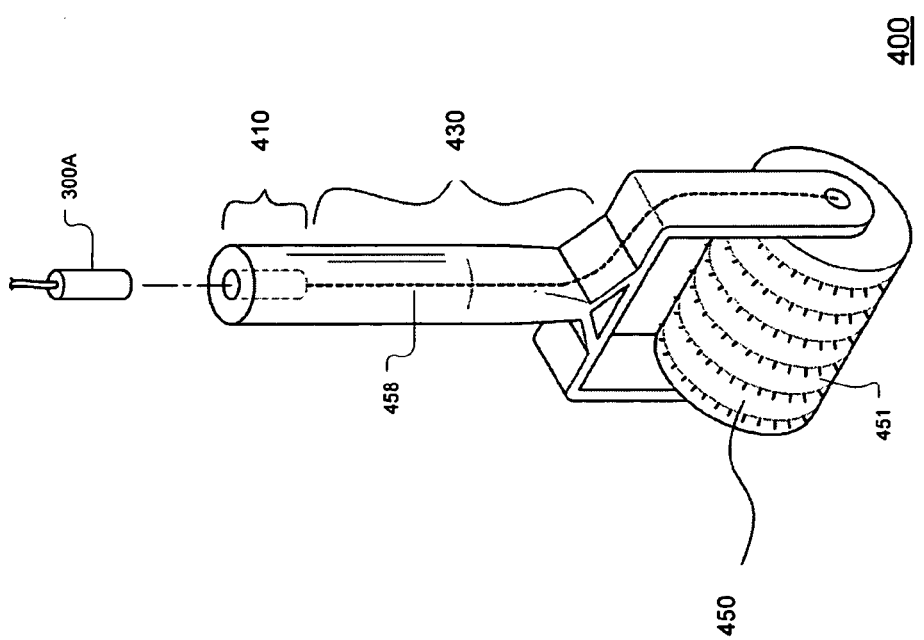
FIG. 3A is a simplified isometric diagram of a dermalogical treatment apparatus according to various embodiments.

FIGS. 3A and 3B are simplified isometric diagrams of acupuncture apparatus 400, 460 including at least one pin 451 that may be coupled to an electrical signal via an internal wire 458. Each apparatus 400, 460 includes curved roller 450 having a plurality of acupuncture pins 451 where the pins 451 may be similar to pins 351. In apparatus 400, the electrical lead wire 400A may be coupled to an electrical interface 410 in the apparatus handle 430 where the interface 410 is electrically coupled to the internal wire 458. In apparatus 460, the handle 430 may include a signal generator 470 similar to generator 370, switch 475, and conduction surface 490. Apparatus 460 may operate similar to apparatus 360 in operation other than the rolling capability of the apparatus 460, 400. In an embodiment the rollers 450 may have various configurations to conform to a dermal area to be treated.

Figure 4B:
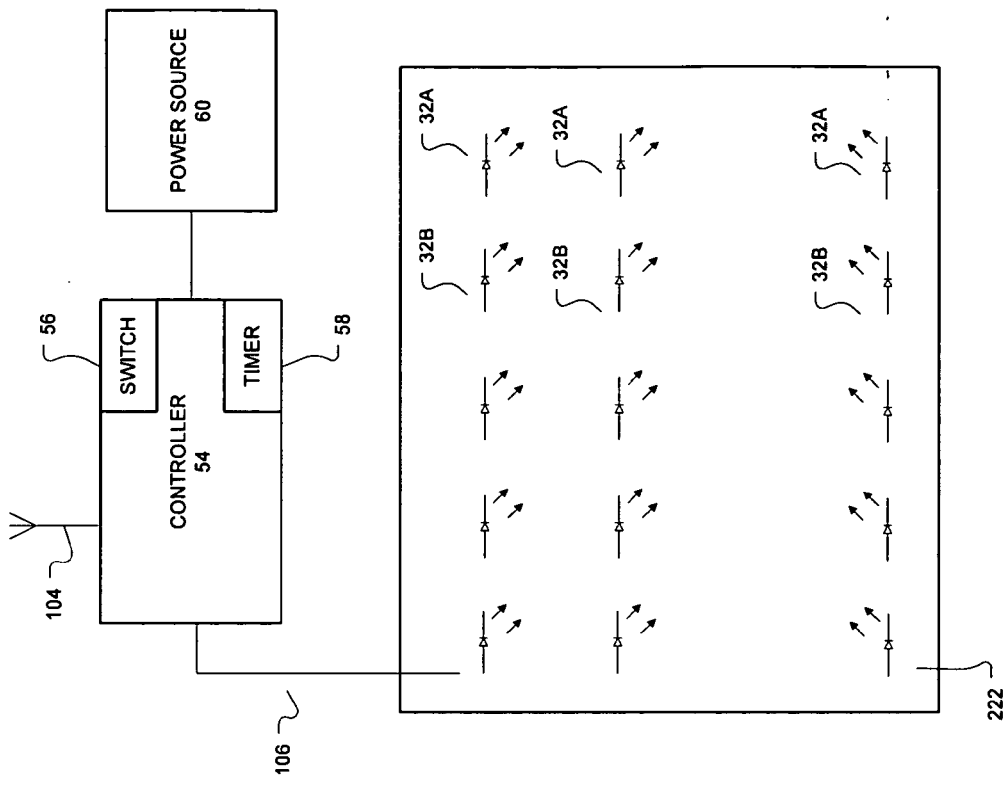
FIG. 4B is a simplified view of a layer and apparatus of a dermalogical treatment system according to various embodiments.
Figure 4A:
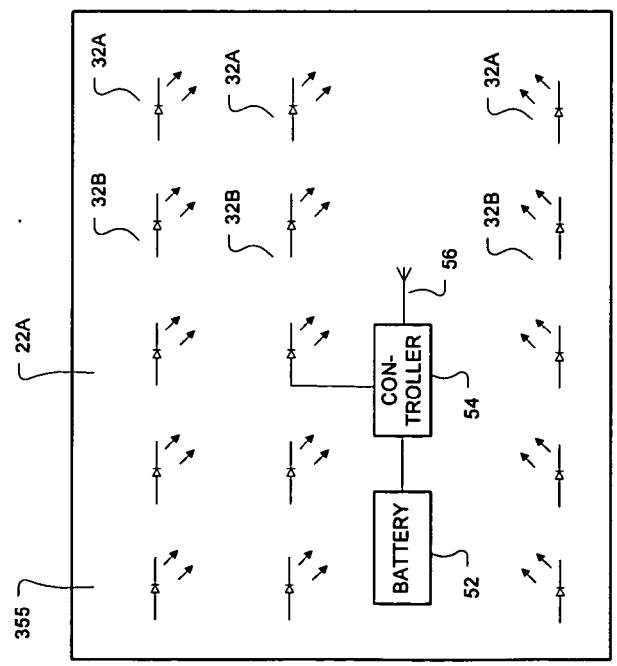
FIG. 4A is a simplified view of a layer of a dermalogical treatment apparatus according to various embodiments.
Figure 4C:
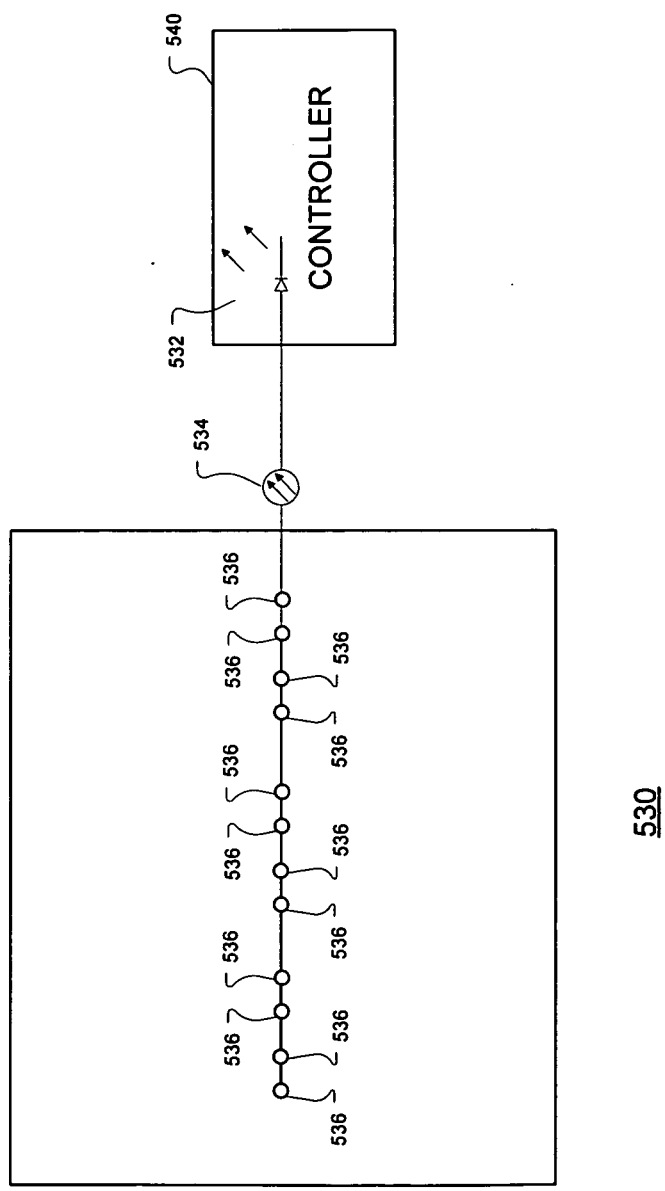
FIG. 4C is a simplified view of a layer and apparatus of a dermalogical treatment system according to various embodiments.

In any of the above apparatus 10, 320, 350, 360, 400, 460, the plate or roller 200, 350, 450 may include a plurality of embedded LEDs 32A, 32B, a battery 52, a controller 54, and an antenna 56 as shown in FIG. 4A. In an embodiment LED 32A may be configured to emit energy of a first particular frequency range and the LED 32B may be configured to emit energy of a second particular frequency range. The surface 22 of a roller 450, plate 200, 350, 450 may also be embedded with a chemical 22A that may be used to treat dermalogical cells. The chemical 22A may be reactive to the first and the second frequency ranges. Further dermalogical cells may be reactive to the first and the second frequency ranges. In addition, the combination of the chemical 22A and the application of the first and the second frequency ranges to the chemical 22A and dermalogical cells may have a synergetic effect.

In an embodiment the chemical 22A may be applied directly to the dermalogical cells to be treated. In a further embodiment a chemical 22A may not be employed in addition to the apparatus 10, 320, 350, 360, 400, 460. In an embodiment the pin section 250, 353, may be translucent and comprised of a polyurethane, medical silicon, or other pliable, translucent, hypoallergenic material.

In an embodiment the local controller 54 and battery 52 may also be embedded in the upper section 290, 357, pin section 230, 351, or the handle 220, 330, or separately between these sections. The controller 54 may be electrically coupled to the one or more LEDS 32A, 32B. The controller 54 may also be coupled to a battery 52. The controller 54 may generate one or more signals for LEDs 32A, 32B as a function of a user switch 75, 56. The signals may vary as a function of the first and second frequency ranges. The controller 54 may include one or more timers 58 that may limit the application of energy to the LEDs 32A, 32B to predetermined time intervals. In an embodiment the controller may also be coupled to an antenna 56 to receive or transmit one or more signals related to the transmission of energy to one or more LEDs 32A, 32B. In an embodiment the system 10 may be configured to treat a particular segment of dermalogical cells such as a face. The apparatus 10 may be configured to conform to a user's anatomy so that emitted light is focused on dermalogical cells. In another embodiment 200, the system 200 may be configured to treat another anatomical region including dermalogical cells on an arm, leg, chest, hands, feet, neck, or other region.

In an embodiment 510 shown in FIG. 4B, a controller 54, an antenna 104, and a power source 60 may be located in external to the apparatus 10, 320, 360. The power source 60 may be coupled to the controller 54. The controller 54 may be coupled to one or more LEDs 32A, 32B via one or more electric wires 106. The controller 54 may generate one or more signals for LEDs 32A, 32B as a function of the user switch 56. The signals may vary as a function of the first and second frequency ranges. The controller 54 may include one or more timers 58 that may limit the application of energy to the LEDs 32A, 32B to predetermined time intervals. In an embodiment the controller may also be coupled to an antenna 104 to receive or transmit one or more signals related to the transmission of energy to one or more LEDs 32A, 32B.

In any of the above apparatus 10, 320, 350, 360, 400, 460, the plate or roller 200, 350, 450 may include a plurality of embedded LED lens 536, a fiber optic pathway 534, and an LED 532. In this embodiment the LED 532 may be coupled to lens 536 via the fiber optic pathway 534. The controller 540 may generate an LED signal via the LED 532 that is transmitted to dermalogical cells via the lens 536 and the fiber optic pathway 534.

FIGS. 5A-5B are diagrams of electrical signal waveforms 650, 630, 640 that may be applied to one or more LEDs 32A, 32B, 532 and to the pins 230, 351, 451 according to various embodiments. The signal waveform 650 includes several square-wave pulses 652, 654, 656 that may be applied to an LED 32A, 32B, 532. Each pulse 652, 654, 656 may a have a similar magnitude and envelope. The waveform 650 may be used to energize an LED 32A, 32B, 532 and to the pins 230, 351, 451 periodically P1 for a predetermined interval T1 where each pulse 652, 654, 656 has a amplitude A1. In an embodiment, A1 may be about 0.1 milliamperes (mA) to 10 mA, the pulse width T1 may be about 100 microsecond (μs) to 500 μs and the period P1 may from 100 ms to 500 ms as a function of the energy required to create capacitance in a liquid. In another embodiment, A1 may be about 0.5 milliamperes (mA) to 5 mA, the pulse width T1 may be about 200 microsecond (μs) and the period P1 may about 250 ms as a function of the energy to drive an LED or cause one or more pins 230, 351, 451 to vibrate.

In FIG. 5B a signal waveform 630 may be applied to a first LED 32A, 32B, 532 module or group and to the pins 230, 351, 451 and a second waveform 640 may be applied or used to energize a second LED 32A, 32B, 532 module and the pins 230, 351, 451, 352. The signal waveform 630 includes several square-wave pulses 632, 634, and 636 and the signal waveform 640 includes several square-wave pulses 642, 644, and 646. Each pulse 632, 634, 636, 642, 644, 646 may a have a similar magnitude and envelope. The waveform 630 may be used to energize a first LED 32A, 32B, 332 module and the pins 230, 351, 451 periodically P1 for a predetermined interval T1 where each pulse 632, 634, 636 has an amplitude A1. The waveform 640 may be used to energize a second LED 32A, 32B, 332 module and the pins 230, 351, 451 periodically P2 for a predetermined interval T2 where each pulse 642, 644, 646 has an amplitude B1. The pulse width T1, T2 may be about 100 microsecond (μs) to 500 μs and the period P1, P2 may from 100 ms to 500 ms as a function of the energy to affect dermalogical cells or chemicals 22A. In another embodiment, A1, A2 may be about 0.5 milliamperes (mA) to 5 mA, the pulse width T1, T2 may be about 200 microsecond (μs) and the period P1, P2 may about 250 ms as a function of the energy required to affect dermalogical cells or chemicals 22A. In an embodiment the pulses 632, 634, 636 do not substantially overlap the pulses 642, 644, 646. In an embodiment T1>T2 and P2 is an integer multiple of P1.

FIG. 6 depicts a waveform 670 that includes multiple pulses 672, 674, 676, 678, 682, and 684 that may not overlap in the time or the frequency domain. In an embodiment each pulse 672, 674, 676, 678, 682, and 684 may have a pulse width T3, and frequency spectrum width F1 and period P3. The pulse 672 is frequency offset from the pulse 674, the pulse 676 is frequency offset from the pulse 678, and the pulse 682 is frequency offset from the pulse 684. The pulses 672, 674, 676, 678, 682, and 684 may be applied to an LED module to affect dermalogical cells or chemicals 22A and the pins 230, 351, 451. Pulses 672, 674 having different frequency spectrums may enable different LED stimulation. In an embodiment the pulses 672, 676, 682 may be applied to a first LED module and the pulses 674, 678, 684 may be applied to a second LED module. The frequency separation between the respective pulses may enable simultaneous energization of a first and a second LED module and the pins 230, 351, 451 and subsequent and independent spectrum generation.

Figure 7C:
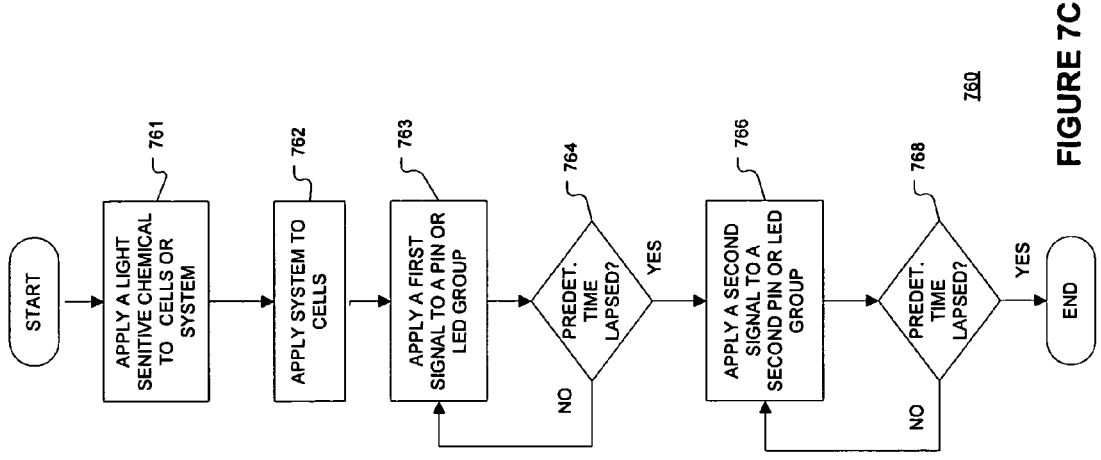
FIG. 7A-7C are flow diagrams illustrating dermalogical treatment system processing algorithms according to various embodiments.
Figure 7B:
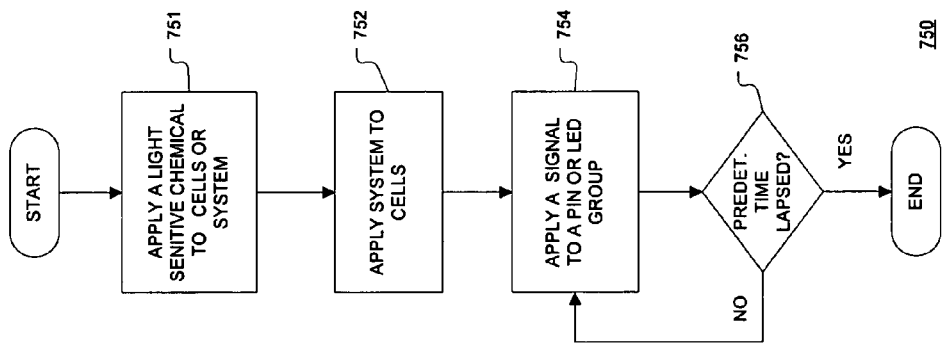
Figure 7A:
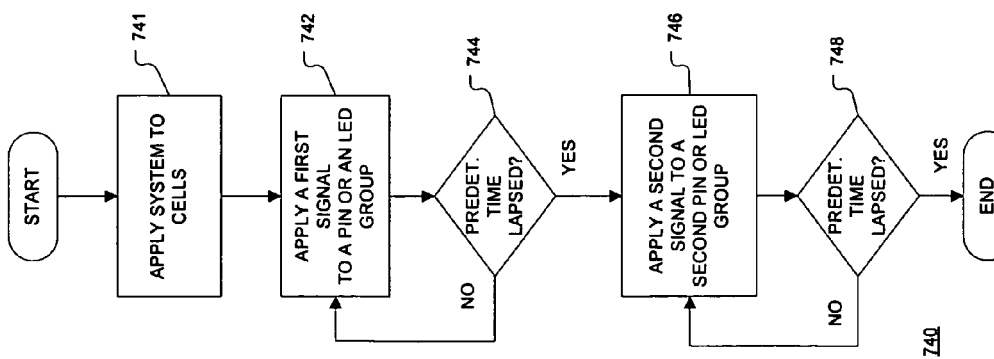

In an embodiment the invention may employ the algorithm 740 shown in FIG. 7A to apply therapy to dermalogical cells. A user, clinician, or equipment may place an apparatus 10, 320, 360, 360, 400, 460 on dermalogical cells to be treated (activity 741) including pressing the apparatus against the cells firmly enough to embed one or more pins 251, 351, 451 in the cells. A first signal such as shown in FIGS. 5A, 5B, and 6 may be applied to a first LED module or group (32A) and the pins 230, 351, 451 of a dermalogical apparatus 10, 320, 360, 360, 400, 460 (activity 742) for a predetermined time period (activity 744). A second signal such as shown in FIGS. 5A, 5B, and 6 may be applied to a second LED module or group (32B) and the pins 230, 351, 451 of a dermalogical apparatus 10, 320, 360, 360, 400, 460 (activity 746) for a predetermined time period (activity 748). The signals applied to the groups may be selected to stimulate dermalogical cells or chemicals 22A or cause vibration of one or more pins 251, 351, 451.

In another embodiment the invention may employ the algorithm 750 shown in FIG. 7B to apply therapy to dermalogical cells. A user, clinician, or equipment may apply a light sensitive chemical on an apparatus 10, 320, 360, 360, 400, 460 or on dermalogical cells to be treated (activity 751). The user, clinician, or equipment may place apparatus 10, 320, 360, 360, 400, 460 on dermalogical cells to be treated (activity 752). A signal such as shown in FIGS. 5A, 5B, and 6 may be applied to a LED module or group (32A or 32B) and the pins 230, 351, 451 (activity 354) for a predetermined time period (activity 356).

In another embodiment the invention may employ the algorithm 760 shown in FIG. 7C to apply therapy to dermalogical cells. A user, clinician, or equipment may apply a light sensitive chemical on an apparatus 10, 320, 360, 360, 400, 460 or on dermalogical cells to be treated (activity 761). The user, clinician, or equipment may place an apparatus 10, 320, 360, 360, 400, 460 on dermalogical cells to be treated (activity 762). A first signal such as shown in FIGS. 5A, 5B, and 6 may be applied to a first LED module or group (32A) and one or more pins 251, 351, 451 of a dermalogical apparatus 10, 320, 360, 360, 400, 460 (activity 763) for a predetermined time period (activity 764). A second signal such as shown in FIGS. 5A, 5B, and 6 may be applied to a second LED module or group (32B) and one or more pins 251, 351, 451 of a dermalogical apparatus 10, 320, 360, 360, 400, 460 (activity 766) for a predetermined time period (activity 768).

The apparatus 10, 320, 360, 360, 400, 460 may be used to employ cosmetic or medications or other chemicals directly on dermalogical cells such as skin with the addition of light of specific frequencies for treatment and healing of epidermal cells of the skin or tissue below the skin with the object of assisting the agents used in delivery, uptake, action and function more effectively. The LEDs 32A, 32B may create the specific frequencies of light. The apparatus 10, 320, 360, 360, 400, 460, light application may enable cosmetic or medication or other active chemicals 22A on dermalogical cells for longer time periods while preventing dehydration of the applied substances. Such light application may improve the efficacy of cosmetic or medication or other active chemical as a function of the selected wavelengths or frequencies.

Further the dermalogical system application may increase cellular activity and help heal tissue faster and facilitate the delivery, uptake and use in the cell of the cosmetics, medications, or chemicals 22A used. The LED light of specific frequencies may increase fibroblast production and collagen as well as other activities of the cell including stimulating the organells and mitochondria to produce ATP for cell energy for functioning, decreasing treatment time and facilitate healing. The apparatus 10, 320, 360, 360, 400, 460 make the agents used on the body more efficacious and useful to the body on a cellular level.

The apparatus 10, 320, 360, 360, 400, 460 may stimulate the basic energy processes in the mitochondria (energy compartments) of each cell, particularly when near-infrared light is used to activate the color sensitive chemicals (chromophores, cytochrome systems) inside but not limited to these spectrum alone as the UV, other visible and IR spectrums may also be usable. In an embodiment optimal LED wavelengths for skin repair may include 640, 680, 730 nanometers (nm) wavelengths to IR 880 nm. Further application of blue light 400 nm to 490 via the apparatus 10, 320, 360, 360, 400, 460 may inhibit the growth and kill bacteria, fungus in and on dermalogical cells. The apparatus 10, 320, 360, 360, 400, 460 may be employed to apply cosmetics, medications and/or other actives directly to the skin and maintain their presence long-term while using LED or other actinic light to increase their effect on the cells and tissue in the body. The apparatus 10, 320, 360, 360, 400, 460 are also highly portability and enable user mobility during treatment.

Chemicals 22A may include cosmetics, medications and other actives appropriate for dermalogical cells including AHA's (alpha hydroxy acid), natural oils, aloe vera compounds, collagen boosters, bt, chitosan, daeses, endorphins, photodynamic drugs (PDT) like (Photofrin or ALA), vitamins A, C E or others, kojic acid, retinols or other exfoliant, salicylic acid, anti oxidants or other youth boosters and anti aging cosmetic or medications, antiseptic, antibiotics, anti-cancer agents, aroma therapy agents, fruit and vegetable extracts, anti-inflammatory agents, pain relievers, hormones, depilatories, and others, but the scope of this invention is not limited to these alone but can include any helpful medication, herbal formula or active compound for the skin and/or other tissues.

Figure 8:
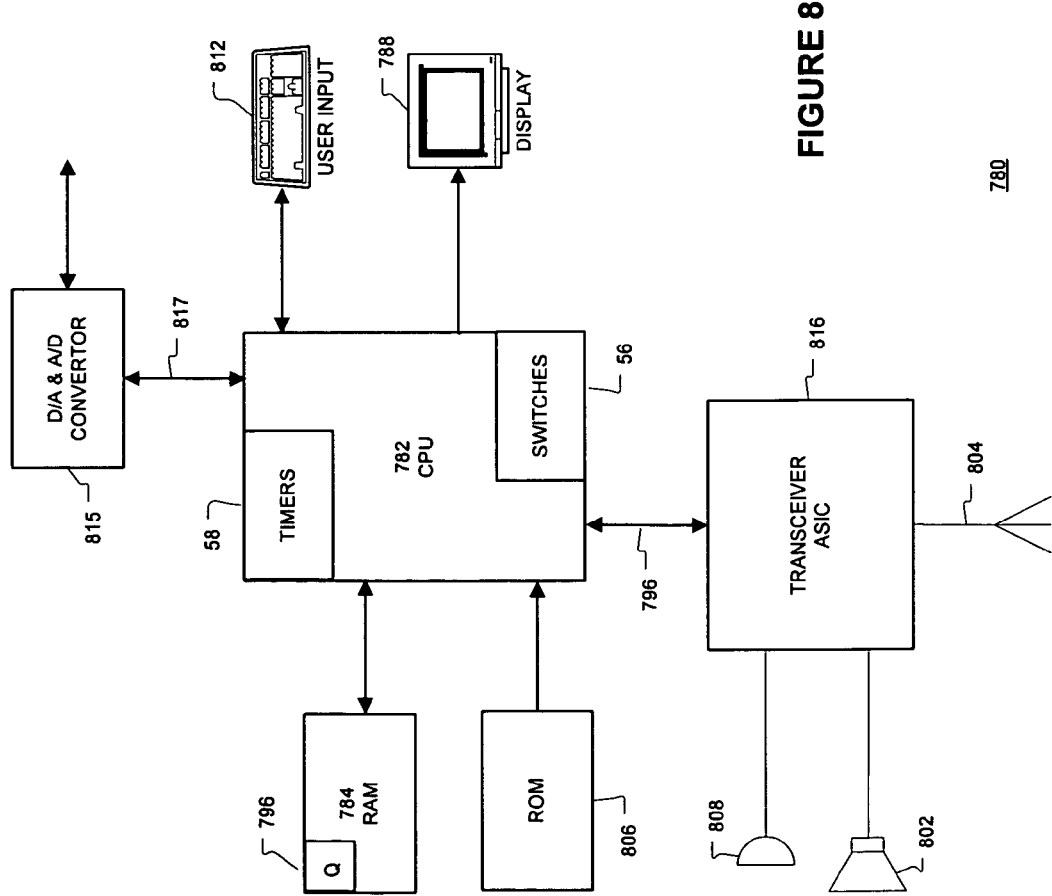
FIG. 8 is a block diagram of an article according to various embodiments.

FIG. 8 is a block diagram of an article 780 according to various embodiments. The article 780 shown in FIG. 8 may be used in various embodiments as a part of apparatus 10, 320, 360, 360, 400, 460 where the article 780 may be any computing device including a personal data assistant, cellular telephone, laptop computer, or desktop computer. The article 780 may include a central processing unit (CPU) 782, a random access memory (RAM) 784, a read only memory (ROM") 806, a display 788, a user input device 812, a transceiver application specific integrated circuit (ASIC) 816, a digital to analog (D/A) and analog to digital (A/D) convertor 815, a microphone 808, a speaker 802, and an antenna 804. The CPU 782 may include an OS module 814 and an application module 813. The RAM 784 may include switches 56 and timers 58.

The ROM 806 is coupled to the CPU 782 and may store program instructions to be executed by the CPU 782. The RAM 784 is coupled to the CPU 782 and may store temporary program data, overhead information, and the queues 798. The user input device 812 may comprise an input device such as a keypad, touch pad screen, track ball or other similar input device that allows the user to navigate through menus in order to operate the article 780. The display 788 may be an output device such as a CRT, LCD, LED or other lighting apparatus that enables the user to read, view, or hear user detectable signals.

The microphone 808 and speaker 802 may be incorporated into the device 780. The microphone 808 and speaker 802 may also be separated from the device 780. Received data may be transmitted to the CPU 782 via a bus 796 where the data may include signals for an LED 32A, 32B, 332 or optical module or wires 331, 458. The transceiver ASIC 816 may include an instruction set necessary to communicate data, screens, or signals. The ASIC 816 may be coupled to the antenna 804 to communicate wireless messages, pages, and signal information within the signal. When a message is received by the transceiver ASIC 816, its corresponding data may be transferred to the CPU 782 via the serial bus 796. The data can include wireless protocol, overhead information, and data to be processed by the device 780 in accordance with the methods described herein.

The D/A and A/D convertor 815 may be coupled to one or more optical modules to generate a signal to be used to energize one of the optical modules. The D/A and A/D convertor 815 may also be coupled to one devices such as LEDs 32A, 32B and the pins 251, 351, 451. Any of the components previously described can be implemented in a number of ways, including embodiments in software. Any of the components previously described can be implemented in a number of ways, including embodiments in software. Thus, the LEDs 32A, 32B, pins 251, 351, 451, controllers 54, switch 56, timers 58, controller 320 may all be characterized as "modules" herein. The modules may include hardware circuitry, single or multi-processor circuits, memory circuits, software program modules and objects, firmware, and combinations thereof, as desired by the architect of the system 10, 30, 50, 60 and as appropriate for particular implementations of various embodiments.

The apparatus and systems of various embodiments may be useful in applications other than a sales architecture configuration. They are not intended to serve as a complete description of all the elements and features of apparatus and systems that might make use of the structures described herein.

Applications that may include the novel apparatus and systems of various embodiments include electronic circuitry used in high-speed computers, communication and signal processing circuitry, modems, single or multi-processor modules, single or multiple embedded processors, data switches, and application-specific modules, including multilayer, multi-chip modules. Such apparatus and systems may further be included as sub-components within a variety of electronic systems, such as televisions, cellular telephones, personal computers (e.g., laptop computers, desktop computers, handheld computers, tablet computers, etc.), workstations, radios, video players, audio players (e.g., mp3 players), vehicles, medical devices (e.g., heart monitor, blood pressure monitor, etc.) and others. Some embodiments may include a number of methods.

It may be possible to execute the activities described herein in an order other than the order described. Various activities described with respect to the methods identified herein can be executed in repetitive, serial, or parallel fashion.

A software program may be launched from a computer-readable medium in a computer-based system to execute functions defined in the software program. Various programming languages may be employed to create software programs designed to implement and perform the methods disclosed herein. The programs may be structured in an object-orientated format using an object-oriented language such as Java or C++. Alternatively, the programs may be structured in a procedure-orientated format using a procedural language, such as assembly or C. The software components may communicate using a number of mechanisms well known to those skilled in the art, such as application program interfaces or inter-process communication techniques, including remote procedure calls. The teachings of various embodiments are not limited to any particular programming language or environment.

The accompanying drawings that form a part hereof show, by way of illustration and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In the foregoing Detailed Description, various features are grouped together in a single embodiment for the purpose of streamlining the disclosure. This method of disclosure is not to be interpreted to require more features than are expressly recited in each claim. Rather, inventive subject matter may be found in less than all features of a single disclosed embodiment. Thus the following claims are hereby incorporated into the Detailed Description, with each claim standing on its own as a separate embodiment.

What is claimed is:

1. A method of treating dermalogical tissue, comprising:
    placing a device including a plurality of pins extending from an inner surface of a distal end of the device on or near dermalogical tissue to be treated with sufficient force to cause at least a first and second adjacent pins of the plurality of pins having a length and shape to penetrate dermalogical tissue; and
    directing a signal generator electrically coupled to the first pin via a first wire and electrically coupled to the second pin via a second wire, forming a dipole pair, and the generator producing a first signal on the first wire for conduction by the first pin and producing a second, different signal on the second wire for conduction by the second, adjacent pin to form a dipole pair to affect dermalogical cells near the dipole pair.

2. The method of claim 1, wherein the first and the second pin of the plurality of pins have a length and shape to enable each pin to penetrate to the derma layer of dermalogical tissue and placing the device with sufficient force to cause the first and the second pin of the plurality of pins to penetrate to the derma layer of dermalogical tissue.

3. The method of claim 2, wherein the first and the second pin of the plurality of pins have a length between 0.5 mm to 1.4 mm and have a diameter from 0.1 to 0.4 mm.

4. The method of claim 3, wherein the first and the second pin of the plurality of pins have a length of about 0.8 mm and have a diameter about 0.3 mm.

5. The method of claim 1, further including directing the signal generator to generate a first signal and a second signal including square wave shaped pulses.

6. The method of claim 1, further comprising directing the signal generator to generate a first signal and a second signal having a pulse width between 100 microseconds and 450 microseconds and a period between 150 microseconds and 500 microseconds.

7. The method of claim 1, further comprising directing the signal generator to generate a first signal and a second signal having a pulse width about 200 microseconds and a period about 250 microseconds.

8. The method of claim 1, wherein the first and second pin form a bipolar pair.

9. The method of claim 1, further comprising directing the signal generator to generate a first signal and a second signal having a current level between 0.5 mA and 5 mA.

10. The method of claim 8, wherein the signal generator generates a first signal on the first wire for conduction by the first pin and to generate a second, different signal on the second wire for conduction by the second pin without a body electrode.

11. An apparatus for treating dermalogical tissue, comprising:
    a device including a plurality of pins extending from an inner surface of a distal end of the device, at least a first and second adjacent pins of the plurality of pins having a length and shape to enable each pin to penetrate dermalogical tissue; and
    a signal generator electrically coupled to the first pin via a first wire and electrically coupled to the second pin via a second wire to form a dipole pair, the generating producing a first signal on the first wire for conduction by the first pin, and producing a second, different signal on the second wire for conduction by the second, adjacent pin to affect dermalogical cells near the dipole pair.

12. The apparatus for claim 11, wherein the first and the second pin of the plurality of pins have a length and shape to enable each pin to penetrate to the derma layer of dermalogical tissue.

13. The apparatus for claim 12, wherein the first and the second pin of the plurality of pins have a length between 0.5 mm to 1.4 mm and have a diameter from 0.1 to 0.4 mm.

14. The apparatus for claim 13, wherein the first and the second pin of the plurality of pins have a length of about 0.8 mm and have a diameter about 0.3 mm.

15. The apparatus for claim 11, wherein the signal generator generates a first signal and a second signal including square wave shaped pulses.

16. The apparatus for claim 11, wherein the signal generator generates a first signal and a second signal have a pulse width between 100 microseconds and 450 microseconds and a period between 150 microseconds and 500 microseconds.

17. The apparatus for claim 11, wherein the first signal and the second signal have a pulse width about 200 microseconds and a period about 250 microseconds.

18. The apparatus for claim 11, wherein the first and second pin form a bipolar pair.

19. The apparatus for claim 11, wherein the first signal and the second signal have a current level between 0.5 mA and 5 mA.

20. The apparatus for claim 11, wherein the signal generator produces a first signal on the first wire for conduction by the first pin and generates a second, different signal on the second wire for conduction by the second pin without a body electrode.

* * * * *